(12) United States Patent
Welz

(10) Patent No.: US 9,329,082 B2
(45) Date of Patent: May 3, 2016

(54) METHOD FOR MEASURING SCATTERED LIGHT AND APPARATUS FOR MEASURING SCATTERED LIGHT

(71) Applicant: Postnova Analytics GmbH, Landsberg (DE)

(72) Inventor: Roland Welz, Schongau (DE)

(73) Assignee: Postnova Analytics GmbH, Landsberg (DE)

( * ) Notice: Subject to any disclaimer, the term of this patent is extended or adjusted under 35 U.S.C. 154(b) by 112 days.

(21) Appl. No.: 14/294,450

(22) Filed: Jun. 3, 2014

(65) Prior Publication Data

US 2014/0354990 A1    Dec. 4, 2014

(30) Foreign Application Priority Data

Jun. 3, 2013  (DE) .......................... 10 2013 210 259

(51) Int. Cl.
*G01J 1/42*      (2006.01)
*G01J 1/08*      (2006.01)
(Continued)

(52) U.S. Cl.
CPC ..... *G01J 1/42* (2013.01); *G01J 1/08* (2013.01); *G01N 15/0205* (2013.01);
(Continued)

(58) Field of Classification Search
USPC ................................. 356/335–343, 244, 246
See application file for complete search history.

(56) References Cited

U.S. PATENT DOCUMENTS 3,659,946 A  *  5/1972  Kozawa ................. G01N 21/51
                                                        250/573
4,907,884 A  *  3/1990  Philips .................... G01N 21/03
                                                        356/336
(Continued)

FOREIGN PATENT DOCUMENTS

DE         4109118        9/1992
DE        19713200        6/1998
(Continued)

OTHER PUBLICATIONS

Peters, ALV-Technical Documentation—ALV-CGS-5022F & ALV-CGS-5050F, ALV-GmbH, Apr. 2, 2001.
(Continued)

*Primary Examiner* — Sang Nguyen
(74) *Attorney, Agent, or Firm* — Hodgson Russ LLP

(57) ABSTRACT

The invention provides a method for measuring light scattered on a sample in a medium, in particular a fluid medium, that comprises the following steps: providing a rotatably arranged measuring cell with a substantially circular cross-section in a plane perpendicular to the axis of rotation for receiving the medium and the sample, rotating the measuring cell, preferably at least once by substantially 360°, about the axis of rotation, in particular by means of a drive, emitting a laser beam by means of a laser onto the sample located within the measuring cell in the plane perpendicular to the axis of rotation at different angles of rotation of the measuring cell, the measuring cell maintaining its position in the direction of the axis of rotation, detecting scattered light signals by means of at least two detectors arranged in a circle and concentrically to the center of rotation of the measuring cell and fixed within set, different angular ranges at different angles of rotation of the measuring cell, and determining a corrected signal value for each detector on the basis of the scattered light signals detected at different angles of rotation of the measuring cell for each detector. Furthermore, the invention provides an apparatus for measuring light scattered on a sample according to the method comprising a laser, a measuring cell and a detector.

22 Claims, 3 Drawing Sheets

Mittelwert = average value
Zeit       = time

(51) Int. Cl.
G01N 15/02 (2006.01)
G01N 21/51 (2006.01)
G01N 21/47 (2006.01)

(52) U.S. Cl.
CPC ........ *G01N 21/51* (2013.01); *G01J 2001/4295* (2013.01); *G01N 2021/4707* (2013.01); *G01N 2021/4711* (2013.01)

(56) References Cited

U.S. PATENT DOCUMENTS

| | | | | |
|---|---|---|---|---|
| 5,129,723 A * | 7/1992 | Howie | ............. | G01N 21/51 356/336 |
| 5,475,235 A * | 12/1995 | Phillips | ............. | H01S 5/042 250/574 |
| 6,118,532 A * | 9/2000 | Peters | ............. | G01J 3/4412 356/338 |
| 6,590,652 B2 * | 7/2003 | Quist | ............. | G01N 15/1456 356/338 |
| 6,774,994 B1 * | 8/2004 | Wyatt | ............. | G01N 21/51 356/336 |
| 7,126,685 B1 | 10/2006 | Paige et al. | | |
| 7,294,513 B2 * | 11/2007 | Wyatt | ............. | G01N 15/0255 356/338 |
| 8,760,652 B2 * | 6/2014 | Frose | ............. | G01N 21/51 356/338 |

FOREIGN PATENT DOCUMENTS

| | | |
|---|---|---|
| DE | 69829812 | 11/2005 |
| EP | 0182618 A2 | 5/1986 |
| EP | 2472219 | 1/2011 |
| EP | 2584353 | 4/2013 |
| WO | 2011088914 | 7/2011 |

OTHER PUBLICATIONS

Peters, ALV-Technical Documentation—ALV / CGS-3, ALV-GmbH, Dec. 21, 2007.

ALV / CGS-8F Compact Goniometer Series—ALV-GmbH, Apr. 9, 2003.

Dogu et al., Influence of observation temperature on light scattering of poly-N-isopropylacrylamide hydrogels, Soft Matter, 2012, 8, pp. 2705-2713.

ALV / CGS-3 Impressions, http://www.alvgmbh.de/Products/goniometers/ALV_CGS3/cgs3imp/cgs3imp.html, Jun. 26, 2008.

ALV-Goniometer Options, http://www.alygmbh.de/Products/goniometers/ALV_CGS8/gonioopt/gonioopt.html, Jun. 26, 2008.

Light Scattering of Polymers and Colloids in Solution, http://www.uni-mainz.de/FB/Chemie/mschmidt/tutorials/sls-dls.html, Feb. 17, 2005.

Instruments, http://www.colloid.ch/grouppage/instruments1.htm, Jan. 1, 2012.

Dynamic Light Scattering, http://www.bzkg.uni-bayreuth.de/de/laboratories/light-scattering/Dynamic_Light_Scattering/index.html, last accessed Oct. 9, 2014.

Photon Correlation Spectroscopy, http://www.chalmers.se/ap/EN/research/condensed-matter-physics/research/equipment-techniques/pcs, last accessed Apr. 12, 2013.

ALV-Products: Goniometer Systems, http://chiwu.chem.cuhk.edu.hk/Facilities/alv/alv-5000.htm, Jan. 7, 2009.

Brookhaven Instruments, BI-200SM, Dynamic and Static Light Scattering System, http://www.brookhaveninstruments.com/pdf/BI-200SM.pdf, last accessed Oct. 9, 2014.

Hardware Manual for the DAWN HELEOS II Light Scattering Instrument, Wyatt Technology Corporation, 2008.

ALV / CGS-8F Goniometer Platform, http://www.alvgmbh.de/Products/goniometers/ALV_CGS8/alv_cgs8.html, Nov. 15, 2009.

LS Spectrometer Data Sheet, LSinstruments, http://www.lsinstruments.ch/_/frontend/handler/document.php?id=263&type=42, last accessed Oct. 9, 2014.

Scattering Goniometer, Homarc Opto-mechatronics Pvt. Ltd., http://holmarc.com/scattering_goniometer.html, last accessed Apr. 16, 2013.

Kulkarni et al., Ergodic and non-ergodic phase transitions in globular protein suspensions, Faraday Discuss., 2003, 123, pp. 37-50. Dec. 16, 2002.

* cited by examiner

1: laser

2: laser beam

3: measuring cell

4: detector

5: scattered light beam

6: rotation apparatus

7: inner aperture system

8: outer aperture system

| Mittelwert | = | average value |
| Zeit | = | time |

Mittelwert = average value
Zeit = time

METHOD FOR MEASURING SCATTERED LIGHT AND APPARATUS FOR MEASURING SCATTERED LIGHT

TECHNICAL FIELD

The invention relates to a method for measuring light scattered on a sample in a medium, in particular a fluid medium, a laser beam being emitted onto a sample located within a measuring cell and the scattered light being detected by a detector. Furthermore, the invention relates to an apparatus for measuring light scattered on a sample in a medium, in particular a fluid medium, according to the method, comprising a laser, a measuring cell and a detector.

PRIOR ART

This type of method is widely used in static light scattering measurement. Static light scattering measurement is used for characterisation with regard to the size, mass, form and structure of molecules or colloidal substances. This is an absolute method which gets by without any previous calibration or use of standard samples.

In order to illustrate the scattering of light, a suspension is observed in which there are a number of macromolecules and which is illuminated with a laser beam. The irradiated light is scattered on each of the macromolecules and the sum of the intensities of the scattered light radiation is in proportion to the concentration of macromolecules in the suspension and to the molar mass of the molecules. The size of the molecules contained in the colloid can be calculated from the angle dependency of the scattered light intensities because the light scattered on the different scatter centres in the macromolecule interferes and generates an angle-dependent scattered light pattern. The average values of the size of the particles located within the measuring cell are respectively determined here.

This type of apparatus for measuring scattered light is known. For example, EP 0 182 618 A2 discloses an apparatus for measuring static light scattering by means of a measuring cell that can be coupled with a chromatographic structure so that the particles, separated according to size, flow through the measuring cell. For this purpose a round glass cell is provided with a longitudinal bore hole through which a liquid flow is conveyed along with the particles that it contains and is illuminated with a laser beam. Detectors which record the scattered light are arranged around the round glass cell at different angles.

Alternatively to the flow-through cells described above, cuvettes are used for batch measurements.

Such measuring systems have proved to be of value. However, ever more stringent demands are being made as regards measuring accuracy. In particular, the measuring cell can be the cause of measuring inaccuracies or errors. On the one hand the measuring cell may be inhomogeneous and/or eccentric. Due to the inhomogeneity and/or eccentricity, diffraction effects may occur at the measuring cell, which deflect the laser beam, by means of which the angle of the irradiated laser light as it enters the measuring cell changes in relation to the respective detector so that the resulting scattering angle no longer corresponds to the detection angle. Until now a so-called index matching bath, which has the same refractive index as the sample glass, has been used for this purpose. The influence of diffraction effects can thus be reduced.

On the other hand, the smallest of impurities in the material of the measuring cell or on the surface of the measuring cell and in the sample itself also lead to detection errors, the impurities being particles with a size in the nm/µm range. In this way, the laser beam is scattered more greatly at the impurities than by the sample, and a signal value that is very prone to error is achieved.

Also the smallest of air pockets in the sample material which are located in the laser's beam path lead to excessive scattering, and this additionally hinders measurement.

DESCRIPTION OF THE INVENTION

It is therefore the object of the present invention to increase measuring accuracy when measuring static light scattering with a simple structure, and in particular to reduce or prevent measuring errors associated with the measuring cell and/or the sample.

According to the invention, this object is achieved by the method having the features of claim 1. Accordingly, the following steps are provided for measuring light scattered on a sample in a medium, in particular a fluid medium: providing a rotatably arranged measuring cell with a substantially circular cross-section in a plane perpendicular to the axis of rotation for receiving the medium and the sample, rotating the measuring cell, preferably at least once by substantially 360°, about the axis of rotation, preferably by means of a drive, emitting a laser beam by means of a laser onto the sample located within the measuring cell in the plane perpendicular to the axis of rotation at different angles of rotation of the measuring cell, the measuring cell maintaining its position in the direction of the axis of rotation, detecting scattered light signals at different angles of rotation of the measuring cell by means of at least two detectors arranged in a circle and concentrically to the centre of rotation of the measuring cell and fixed within set, different angular ranges and determining a corrected signal value for each detector on the basis of the scattered light signals detected at different angles of rotation of the measuring cell for each detector.

Furthermore, according to the invention an apparatus is provided with the features of claim 6. Consequently, the apparatus for measuring light scattered on a sample in a medium, in particular a fluid medium, has a measuring cell that can be rotated about 360° and that is attached in a fixed manner in the direction of the axis of rotation and which has a substantially circular cross-section in a plane perpendicular to the axis of rotation for receiving the medium with the sample, a drive for rotating the measuring cell by 360° about the axis of rotation, a laser for emitting a laser beam onto the measuring cell in the plane perpendicular to the axis of rotation, and at least two detectors that are attached in a fixed manner in a circle and concentrically to the centre of rotation of the measuring cell in order to detect light scattered on the sample at different angles of rotation of the measuring cell within set, different angular ranges.

The idea forming the basis of the invention is to rotate the measuring cell during the measurement, by means of which inhomogeneities and/or eccentricities of the measuring cell and impurities in the material of the measuring cell, on the surface of the measuring cell and in the medium in which the sample is to be found, move into the laser beam and out of the laser beam again during the rotation. By detecting scattered light signals at different angles of rotation of the measuring cell, a corrected signal value can be determined that is calculated on the basis of the scattered light signals detected at different angles of rotation of the measuring cell, which may be subject to error.

In particular, signal peaks caused by impurities—so-called peaks or spikes—can be disregarded on the basis of the plurality of scattered light signals detected at different angles of rotation so that a corrected signal value can be determined.

This enables less elaborate storage or cleaning of the measuring cell. Excessive scattered light signals, which result from (the smallest of) air pockets in the measuring cell material or in the sample, can also be corrected in this way. By means of the present invention the measurement is therefore simplified because, for example, the samples require less elaborate preparation.

Thus, by rotating the measuring cell during the measurement and by detecting scattered light signals at different angles of rotation of the measuring cell, the accuracy and reproducibility of the signal value can be considerably improved.

If the measuring cell is rotated at least once by substantially 360° about the axis of rotation, deviations of the measuring cell from the ideal form can moreover be corrected.

In particular, the measuring cell with the substantially circular cross-section is a measuring cell in the form of a straight circular cylinder, the cross-section of which can deviate in the µm range from an ideal circle or the wall thickness of which can deviate in the µm range from an ideal circle. Since these deviations are in the µm range, this type of cross-section is called circular, even if there is no ideal circle on the µm plane. The ideal form of the measuring cells is in particular to be understood as being the form on the µm plane which would have to be present in order for there to be an ideal circular form with µm accuracy.

If the measuring cell deviates from an ideal circular cross-section with a constant wall thickness, the laser beam does not pass in a straight line through the measuring cell, but it is deflected at a different angle on the wall of the measuring cell so that a scattered light signal that is too high or too low is detected dependently upon the diffraction angle at a given detection angle.

For example, upon rotating a measuring cell with a cross-section deviating from an ideally circular cross-section, during a rotation by 360° the laser beam can be diffracted once towards the respective detection angle and once (after a 180° rotation) away from the detection angle, by means of which a sinusoidal detection signal is produced for the respective detection angle which oscillates by a value that corresponds to the corrected average value.

The rotation is implemented by a drive, in particular a motor. Here the measuring cell is attached in a fixed manner in the direction of the axis of rotation and the drive does not allow any movement of the measuring cell in the direction of the axis of rotation. In one embodiment the measuring cell is attached within a rotation apparatus arranged concentrically to the axis of rotation and into which the measuring cell is introduced from above.

The laser beam, the measuring cell and the detectors are arranged in a plane here.

The measuring cell is produced, for example, from glass or polymer and has a refractive index which corresponds substantially to the refractive index of the medium and which is higher than the refractive index of air. The measuring cell is preferably produced from glass and particularly preferably from quartz glass or borosilicate glass.

The apparatus does not have any additional device for preventing reflections of the laser beam on the surface of the measuring cell, and in particular does not have any device for adapting to the refractive index of the measuring cell, such as for example an index matching bath.

The medium in which the sample is located is in particular, i.e. preferably, a fluid, and particularly preferably, a liquid medium that is not a non-ergodic medium, and in particular is not a gel. The sample is distributed substantially homogeneously within the medium. The medium in which the sample is dissolved or suspended can be an aqueous or non-aqueous organic solvent.

Light scattered on the sample (scattered light) is produced by means of a laser beam with which the sample located within the measuring cell is illuminated, the coherence length of the laser beam preferably being greater than the maximum size of the sample to be measured. Different lasers, such as e.g. diode lasers, solid state lasers or glass lasers, can be used as the laser beam source. Preferably, lasers with a wavelength of 245 nm to 1200 nm, preferably of 375 nm to 1064 nm and more preferably of 320 nm to 680 nm are used. Particularly preferably, lasers with a wavelength of 532 nm are used.

In particular, a detector is to be understood to be a light-sensitive diode or a photomultiplier. Hybrid photodiodes are particularly preferred, these being a combination of a photodiode with an integrated amplifier.

The detectors are arranged in fixed, different angular ranges of 7° to 164° and thus make it possible to observe scattered light in fixed, different angular ranges of 7° to 164°.

The term "angular range" designates a specific angle in relation to the beam path of the laser through the measuring cell within the detection plane, including a range around this angle of +/−0.95° and preferably of +/−0.15°.

The apparatus has at least two, preferably up to 25, more preferably 7 to 21, and particularly preferably 21 detectors. 7 or 14 detectors can also be provided. In one embodiment the apparatus has 2 to 25, preferably 7 to 21 and particularly preferably 7, 14 or 21 detectors.

During the rotation of the measuring cell by 360°, scattered light signals are detected simultaneously at all of the detectors. The signals are detected by the detectors every 10-1000 ms, preferably every 50-100 ms and particularly preferably every 60 ms.

During the measurement or the detection of the scattered light signals, the sample is preferably rotated continuously. The measuring cell rotates at least once or a number of times by substantially 360° during the measurement. The rotation speed is preferably in a range of 1 to 100 rev/min here, preferably in a range of 1 to 50 rev/min and particularly preferably in a range of 20 to 30 rev/min, preferably 25 rev/min. Even more preferably the rotation speed is 3 rev/min.

If scattered light signals are detected by the detectors, for example, every 60 ms, the angular increment is preferably in a range of 0.36 to 36°, preferably in a range of 0.36 to 18°, particularly preferably in a range of 7.2 to 10.8° and in particular preferably 9°. Even more preferably, the angular increment is 1.08°.

Alternatively, the rotation can also take place step by step, the scattered light signals then being detected during a temporary standstill of the measuring cell and the respectively detected scattered light signals being able to be assigned to a different angle of rotation of the measuring cell.

It is evident that the measuring accuracy is increased if the number of rotation angles at which a scattered light signal is detected is increased.

The direction of rotation can be chosen freely; during a measurement, however, a full rotation at least once by substantially 360° is preferably to be executed, i.e. preferably no change to the direction of rotation should be made during a measurement.

Particularly advantageous further developments of the invention are specified in the dependent claims.

According to the method, the signal value detected by each detector can be corrected such that scattered light signals, which result from the deviation of the design of the measuring cell from its ideal form and/or from defects in the material of the measuring cell and/or from impurities on the surface of the measuring cell and/or in the medium in which the sample is located, are not taken into account. The individual scattered light signals, which are detected by a detector at different angles of rotation of the measuring cell, can be stored intermediately and be processed so that scattered light signals which would lead to an incorrect measurement can be disregarded and a corrected signal value can be specified. The apparatus according to the invention accordingly has a control unit which is set up to control the apparatus such that the measuring cell is rotated at least once by substantially 360° during the measurement, scattered light signals are detected by each detector at different angles of rotation of the measuring angles and, on the basis of the scattered light signals detected by each detector at different angles of rotation of the measuring cell a corrected signal value is determined by each detector.

It is also preferable if the signal value is corrected if the design of the measuring cell deviates from its ideal form by forming the average value of the scattered light signals detected by each detector at different angles of rotation of the measuring cell with a rotation at least once by substantially 360° and the signal value is corrected if there are defects in the material in the measuring cell and/or if there are impurities on the surface of the measuring cell and/or in the medium in which the sample is located by adapting individual detected scattered light signals on the basis of a comparison of scattered light signals at consecutive angles of rotation of the measuring cell, in particular by smoothing spikes. The control unit of the apparatus according to the invention is accordingly set up to correct the signal value such that scattered light signals, which result from the deviation of the design of the measuring cell from its ideal form and/or from defects in the material of the measuring cell and/or from impurities on the surface of the measuring cell and/or in the medium in which the sample is located, are not taken into account.

Before the measurement, the sample can be separated by means of a chromatographic or a quasi-chromatographic separating method into individual fractions each with a substantially uniform particle size and/or each with a substantially uniform molar mass.

Preferably, the sample separation is implemented here by means of HPLC (High Performance Liquid Chromatography), in particular Size Exclusion Chromatography (SEC) or Gel Permeation Chromatography (GPC), or by means of Field-Flow Fractionation (FFF).

A batch measurement or a flow-through measurement (on-line measurement) can be taken here, and so the measuring cell is accordingly a cuvette or a flow-through cell.

Furthermore, the apparatus can have at least one aperture system (7, 8) that is arranged between the measuring cell (3) and the detectors (4). In particular, a first inner aperture system (7) and a second outer aperture system (8) can be provided, the detectors (4) being arranged outside of the second outer aperture system (8) and the first inner aperture system (7) and the second outer aperture system a) being arranged in a circle and concentrically to the centre of rotation of the measuring cell (3). In this connection reference is made to the disclosure of EP 2 584 353 A1 which discloses this type of aperture system.

The apparatus serves to measure light scattered on the sample located in the medium, in particular a fluid medium, in particular by means of a batch measurement or an online measurement.

Further features and advantages of the invention become more apparent by means of the detailed description given below.

DETAILED DESCRIPTION OF A PREFERRED EMBODIMENT

One preferred embodiment of the present invention is described in detail below with reference to the accompanying drawings.

Figure 1:
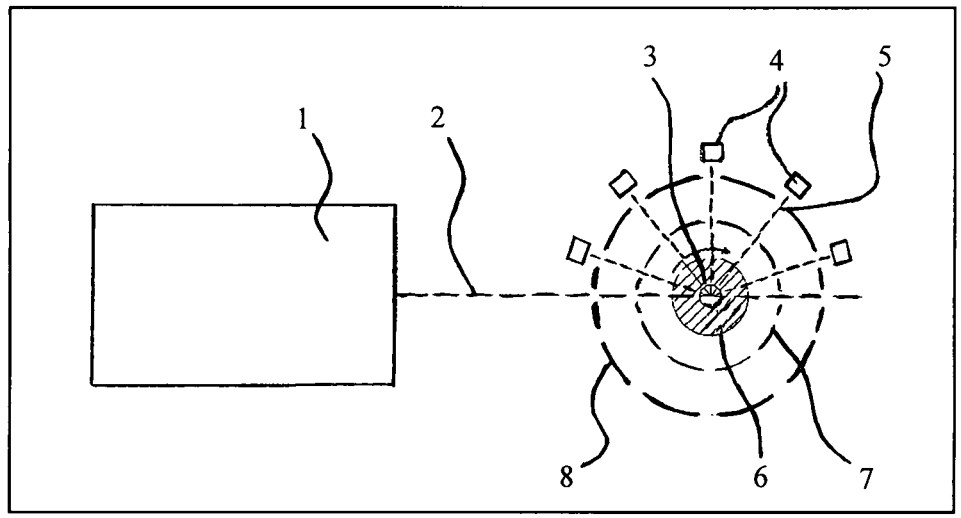
FIG. 1 shows an apparatus according to the invention.

FIG. 1 shows the diagrammatic structure of an apparatus according to the invention in a top view. The apparatus has a laser (1), a cylindrical measuring cell (3) and detectors (4) which are arranged in a circle and concentrically around the axis of rotation of the measuring cell (3), fixed at set, different angles. The axis of rotation of the measuring cell (3) runs through the centre point of the measuring cell (considered in a cross-section or the top view of FIG. 1). The measuring cell (3) is arranged in a rotation apparatus (6) so that the measuring cell (3) can rotate relative to the fixed detectors (4). For example, five detectors (4) are shown in FIG. 1.

For the measurement, a laser beam (2) is emitted by the laser (1) onto the measuring cell (3) and is scattered on the sample located therein. The detectors (4) detect scattered light (5).

A drive (not shown) is located on, below or above the rotation apparatus (6) in which the measuring cell (3) is arranged.

An aperture system 7, 8, preferably consisting of a first inner ring 7 and a second outer ring 8, can be arranged between the measuring cell (3) and the detectors (4).

Figure 2A:
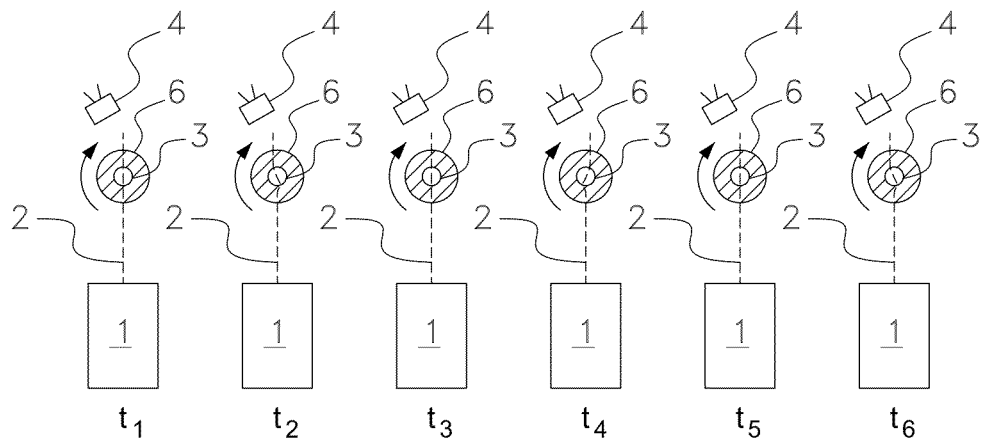
FIGS. 2 (a) and 2 (b) show a chart illustrating the principle of the present invention.
Figure 2B:
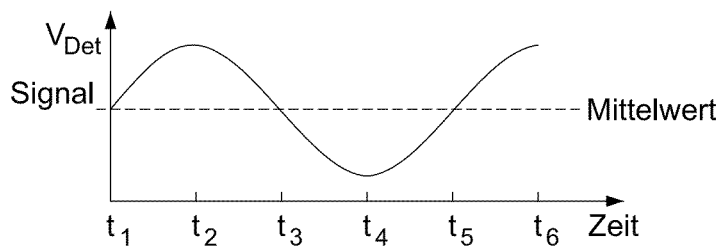

FIGS. 2(a) and 2(b) illustrate diagrammatically the basic idea behind the present invention. According to FIG. 2(a), light is irradiated at times $t_1$ to $t_6$ at a specific angle of rotation of the measuring cell (3) by means of a laser beam (2). Simultaneously, the scattered light (not shown in FIG. 2(a)) is detected in the detector (4) at times $t_1$ to $t_6$, at each time $t_i$ there being a different angle of rotation of the measuring cell or a rotation of the measuring cell having taken place between the times $t_i$, for i=1 to 6 in this example. Thus for example, at a time $t_1$ a scattered light signal that is not subject to error can be detected. With a further rotation of the measuring cell (3), at time $t_2$ the laser beam (2) from the measuring cell (3) is deflected to the left from the original direction of the laser beam (2) due to a deviation of the measuring cell from its ideal form, as specified in FIG. 2(a) at time $t_2$. In this way a scattered light signal, that is accordingly subject to error, is detected at time $t_2$. At time $t_3$, the measuring cell has rotated by 180° in comparison to time $t_1$, and no deflection of the laser beam (2) takes place. At time $t_4$, which differs from time $t_2$ by a 180° rotation, the laser beam (2) is deflected by the measuring cell (3), as specified at time $t_4$ in FIG. 2(a), from the original direction of the laser beam (2) to the right. The deflection of the laser beam (2) at time $t_2$ is opposite to the deflection of the laser beam (2) at time $t_4$. As a result, the laser beam (2) is deflected due to the deviation of the measuring cell from its ideal form towards a respective detector and away from a respective detector so that scattered light signals that are accordingly subject to error are detected by the respective detector. The angle of rotation of the measuring cell, i.e. the position of the measuring cell at times $t_5$ and $t_6$, corresponds to the angle of rotation of the measuring cell at times $t_1$ and $t_2$.

Due to the interaction between the laser beam (2) and the measuring cell (3) shown in FIG. 2(a), the temporal profile of the scattered light signal which is based on the voltage measured in the detector (4) and is shown in FIG. 2(b) is produced. A sinusoidal or cosinusoidal temporal profile of the scattered light signal is produced for each detector around an average value. This average value corresponds to the signal value of the scattered light.

FIG. 3 illustrates the idea behind the invention in further detail, in particular with regard to the presence of signal peaks (spikes) in connection with impurities on or in the measuring cell.

Figure 3A:
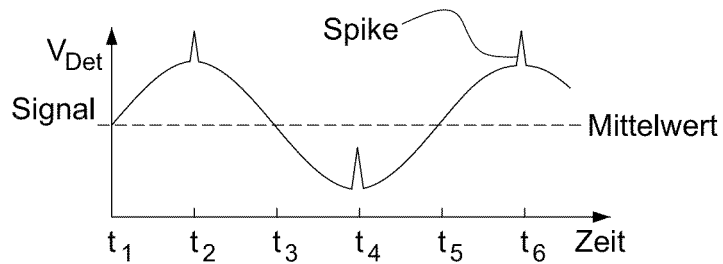
FIGS. 3 (a) to 3 (c) show a further chart illustrating the principle of the invention.

During times $t_1$ $t_3$ and $t_5$, the laser beam or a scattered light beam does not strike any impurity, as shown in FIG. 3(a). In contrast, at times $t_2$, $t_4$ and $t_6$ there is an impurity in the laser beam and/or in the scattered light beam and thereby causes a strong signal rise—a so-called spike.

Figure 3B:
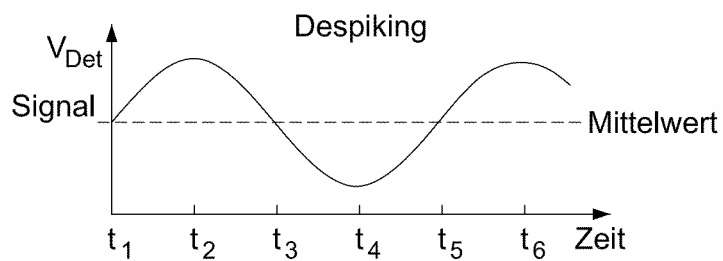
Figure 3C:
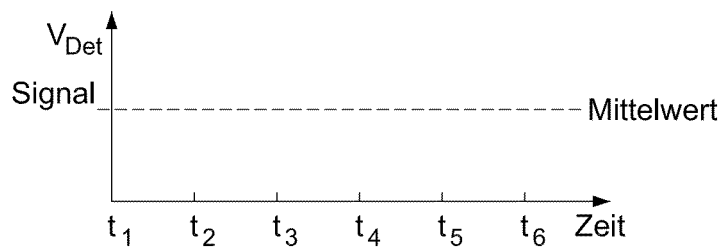

Despiking is first of all carried out, a minimum value assessment being made so that the spikes can be removed calculatively from the sinus signal, as shown in FIG. 3(b). Next, the average value of the sinus curve is calculated, and so the corrected signal value which is shown in FIG. 3(c) is obtained.

The invention claimed is:

1. A method for measuring light scattered on a sample in a medium, in particular a fluid medium, comprising the following steps:
   providing a rotatably arranged measuring cell (3) with a substantially circular cross-section in a plane perpendicular to the axis of rotation for receiving the medium and the sample,
   rotating the measuring cell about the axis of rotation,
   emitting a laser beam (2) onto the sample located within the measuring cell (3) in the plane perpendicular to the axis of rotation at different angles of rotation of the measuring cell, the measuring cell maintaining its position in the direction of the axis of rotation,
   providing at least two detectors (4) fixed relative to the laser beam and arranged in a circle concentrically to the centre of rotation of the measuring cell and fixed within set, different angular ranges,
   using the at least two detectors to detect scattered light signals at different angles of rotation of the measuring cell; and
   determining a corrected signal value for each detector on the basis of the scattered light signals detected at different angles of rotation of the measuring cell for each detector.

2. The method according to claim 1, wherein the signal value is corrected such that scattered light signals, which result from a design deviation of the measuring cell from a desired form or from defects in the material of the measuring cell or from impurities on the surface of the measuring cell (3) or in the medium in which the sample is located, are not taken into account.

3. The method according to claim 1, wherein the signal value is corrected if the design of the measuring cell (3) deviates from a desired form by forming the average value of the scattered light signals detected by each detector (4) at different angles of rotation of the measuring cell with a rotation at least once by substantially 360° and the signal value is corrected if there are defects in the material of the measuring cell or if there are impurities on the surface of the measuring cell or in the medium in which the sample is located by adapting individual detected scattered light signals on the basis of a comparison of scattered light signals at consecutive angles of rotation of the measuring cell, in particular by smoothing spikes.

4. The method according to claim 1, wherein the sample has a substantially uniform particle size or a substantially uniform molar mass as a result of applying a chromatographic separating method.

5. The method according to claim 4, wherein the chromatographic separating method is an HPLC method, in particular size exclusion chromatography (SEC).

6. The method according to claim 4, wherein the chromatographic separating method is an HPLC method, in particular gel permeation chromatography (GPC).

7. The method according to claim 1, wherein the sample has a substantially uniform particle size or a substantially uniform molar mass as a result of applying a quasi-chromatographic separating method.

8. The method according to claim 7, wherein the quasi-chromatographic separating method is a field-flow fractionation method.

9. An apparatus for measuring light scattered on a sample in a medium, in particular a fluid medium, the apparatus comprising:
   a measuring cell (3) arranged to be rotatable about an axis of rotation and arranged in a fixed manner in the direction of the axis of rotation and which has a substantially circular cross-section in a plane perpendicular to the axis of rotation for receiving the medium with the sample,
   a drive for rotating the measuring cell by 360° about the axis of rotation,
   a laser (1) for emitting a laser beam (2) onto the measuring cell in the plane perpendicular to the axis of rotation, and
   at least two detectors (4) that are attached in a fixed manner relative to the laser beam and in a circle concentrically to the centre of rotation of the measuring cell in order to detect light scattered on the sample at different angles of rotation of the measuring cell within set, different angular ranges.

10. The apparatus according to claim 9, wherein the measuring cell (3) is a measuring cell for batch measurements, in particular a cuvette.

11. The apparatus according to claim 9, arranged such that when the measuring cell (3) is rotated at least once by substantially 360° during the measurement, scattered light signals are detected by each detector (4) at different angles of rotation of the measuring cells and a corrected signal value is determined by each detector on the basis of the scattered light signals detected by each detector at different angles of rotation of the measuring cell.

12. The apparatus according to claim 11, arranged such that for determining a corrected signal value scattered light signals, which result from a design deviation of the measuring cell (3) from a desired form or from defects in the material of the measuring cell or from impurities on the surface of the measuring cell or in the medium in which the sample is located, are not taken into account.

13. The apparatus according to claim 9, which has at least one aperture system.

14. The apparatus according to claim 13 which has a first inner aperture system and a second outer aperture system, wherein the detectors (4) are arranged outside of the second outer aperture system and wherein the first inner aperture system and the second outer aperture system are arranged in a circle concentrically to the centre of rotation of the measuring cell (3).

15. The apparatus according to claim 9, wherein the detectors (4) are arranged in fixed, different angular ranges of 7° to 164° in relation to the beam path of the laser (1) through the measuring cell (3).

16. The apparatus according to claim 9, which has 2 to 25 detectors (4).

17. The apparatus according to claim 9, which has 7 to 21 detectors (4).

18. The apparatus according to claim 9, which has 7, 14 or 21 detectors (4).

19. The apparatus according to claim 9, wherein the measuring cell (3) is a flow-through cell.

20. A method for measuring light scattered on a sample located in a medium, in particular a fluid medium, comprising:
    providing an apparatus having:
        (a) a measuring cell (3) that can be rotated about 360° and that is attached in a fixed manner in the direction of the axis of rotation and which has a substantially circular cross-section in a plane perpendicular to the axis of rotation for receiving the medium with the sample,
        (b) a drive for rotating the measuring cell by 360° about the axis of rotation,
        (c) a laser (1) for emitting a laser beam (2) onto the measuring cell in the plane perpendicular to the axis of rotation, and
        (d) at least two detectors (4) that are attached in a fixed manner relative to the laser beam in a circle concentrically to the centre of rotation of the measuring cell in order to detect light scattered on the sample at different angles of rotation of the measuring cell within set, different angular ranges;
    using the apparatus to measure light scattered on the sample located in the medium, in particular a fluid medium.

21. The method of claim 20, wherein the measurement of light scattered on the sample is taken in batches.

22. The method of claim 20, wherein the measurement of light scattered on the sample is an online measurement.

* * * * *